United States Patent [19]

Jordan

[11] Patent Number: 5,426,026
[45] Date of Patent: Jun. 20, 1995

[54] PCR IDENTIFICATION OF FOUR MEDICALLY IMPORTANT CANDIDA SPECIES USING ONE PRIMER PAIR AND FOUR SPECIES-SPECIFIC PROBES

[75] Inventor: Jeanne A. Jordan, Pittsburgh, Pa.

[73] Assignee: University of Pittsburgh, Pittsburgh, Pa.

[21] Appl. No.: 120,780

[22] Filed: Sep. 15, 1993

[51] Int. Cl.$^6$ .................................................. C12Q 1/68
[52] U.S. Cl. ...................................... 435/6; 536/24.32; 536/23.74; 435/255.4; 435/91.2
[58] Field of Search ................... 435/6, 255.4, 91.2; 536/24.32, 23/74

[56] References Cited

PUBLICATIONS

GenBank Accession No. X5242, C. albicans CHSI gene for chitin synthase, Nov. 13, 1991.
Lehmann et al. J. Clinical Microbiology, 30(7):3249–3254, Dec. 1992.

*Primary Examiner*—Margaret Parr
*Assistant Examiner*—Scott W. Houtteman
*Attorney, Agent, or Firm*—Cushman Darby & Cushman

[57] ABSTRACT

The subject invention relates to A set of DNA primers which, when utilized in conjunction with the polymerase chain reaction (PCR) assay, can amplify and speciate DNA from four medically important Candida species. Furthermore, the PCR amplified products, generated by the primers, can also be used to create species specific probes which can also detect and confirm the four species of Candida. Thus, the present invention allows for early diagnosis and treatment of an infection.

12 Claims, 2 Drawing Sheets

FIG. I
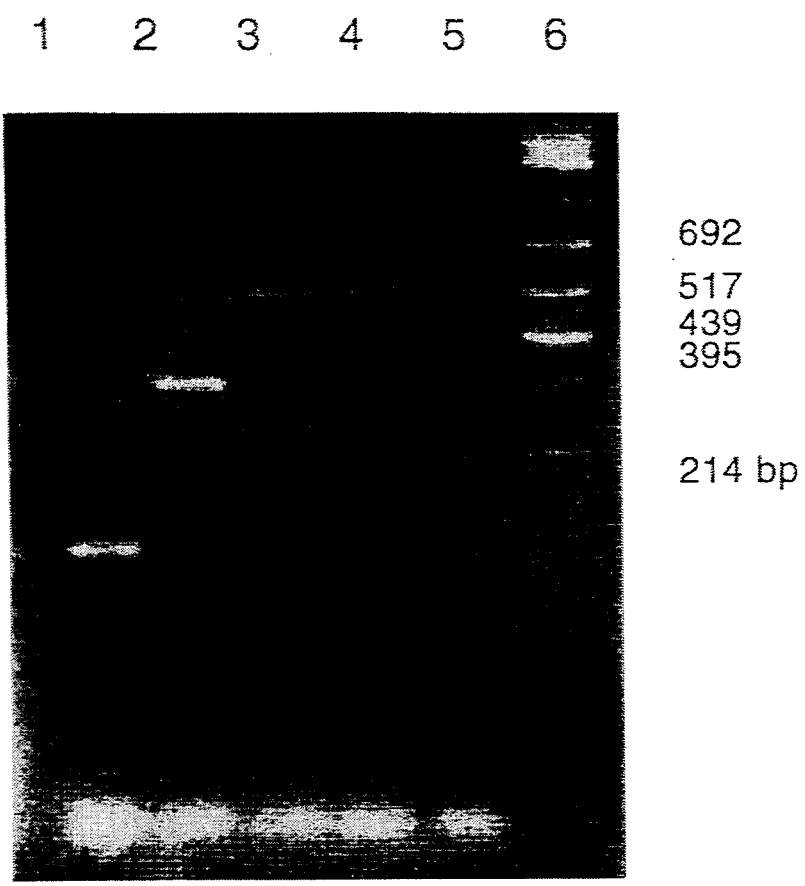

PCR IDENTIFICATION OF FOUR MEDICALLY IMPORTANT CANDIDA SPECIES USING ONE PRIMER PAIR AND FOUR SPECIES-SPECIFIC PROBES

BACKGROUND OF THE INVENTION

1. Field of the Invention

The subject invention relates to a set of DNA primers which, when utilized in conjunction with the polymerase chain reaction (PCR) assay, can amplify and speciate DNA from four medically important Candida species. Furthermore, the PCR amplified DNA products generated by the primers can be sequenced, and the sequence information can be used to create species-specific probes which can confirm these four species of Candida. Thus, the primers and probes of the present invention allow for earlier diagnosis and treatment of an infection compared to diagnosis and treatment resulting from the standard method of routine culturing.

2. Background Information

Diagnosing systemic Candida infection continues to be a major challenge for the clinician. This is especially true in the low birth weight (VLBW) neonate where, historically, 30% of all neonatal systemic Candidiasis is not diagnosed until autopsy ("Systemic Candidiasis" In *Candidiasis*, eds., Bodey et al., Raven Press, N.Y. (1985)). The difficulty in diagnosing neonatal candidemia is due, in part, to the lack of a sensitive detection system and to the minimal blood volume that can be obtained for testing. Currently, the gold standard for diagnosing systemic candidiasis is to recover the organism by routine blood culturing (Kiehn et al., *J. Clin. Microbiol* 14:681-83 (1981); Roberts et al., *J. Clin. Microbiol.* 1:309-10 (1975)). This technique is not always satisfactory in detecting infection early, a critical point for successful outcome in treating systemic candidiasis. In fact, 40-60% of all blood cultures remain negative for Candida despite widespread visceral infection ("Systemic Candidiasis" In *Candidiasis*, eds., Bodey et al., Raven Press, N.Y. (1985)).

Furthermore, in addition to the time required to grow the yeast from blood culture, additional time is necessary in which to identify and speciate the organism. All of this testing can become a very lengthy process, leaving the infection unchecked in the patient, leading to an increased fungal load.

Unlike the comparative safety of antibiotics, antifungal drugs are quite toxic. Therefore, physicians usually require substantial documentation of fungal infection before they are willing to initiate antifungal therapy. Prompt detection of candidiasis would enable earlier treatment initiation on a smaller fungal load. Thus, timely detection and speciation of Candida infections is crucial for reducing morbidity and mortality especially in the premature newborn and the immunosuppressed population (i.e., bone marrow transplant patients, AIDS patients, etc.).

It is the amplification property of the polymerase chain reaction (PCR) assay together with its short turnaround time that makes it ideal for diagnosing candidemia from even minimal blood volumes. PCR is an efficient, in-vitro method for amplifying DNA from clinical samples that can be tailor-made to suit the needs of any diagnostic laboratory (see U.S. Pat. No. 4,683,202 and U.S. Pat. No. 4,683,195). Buchman et al. was the first group to describe the use of PCR to identify Candida albicans from clinical specimens. These investigators used PCR to amplify a portion of a yeast-specific gene *cytochrome lanosterol-14α-demethylase* (Buchman et al., Surgery 108:338-47 (1990)).

More specifically, Buchman et al. utilized a set of primers that amplified the Candida albicans cytochrome $P_{450}$ $L_1A_1$ (lanosterol-14α-*demethylase*) gene. The predicted product size was estimated to be 240 base pairs. However, aberrant and unexplained amplification patterns were seen in various clinical specimens containing C. albicans DNA.

In addition, the primer set utilized by Buchman et al. amplified DNA from other non-albicans species giving rise to some PCR products of the "predicted" 240 bp size and some of an alternate size. Other non-albican species gave no 240 bp fragment but just a variety of alternate-sized products. There was no consistency in the size of the PCR products generated using this primer set.

SUMMARY OF THE INVENTION

The present invention relates to a sensitive and rapid assay which can be used to detect Candida albicans (as well as three other Candida species) in the blood of neonates. A single pair of DNA primers was designed from the published sequence of the *chitin synthase* gene CHS1 of Candida albicans (Au-Young et al, Mol. Microbiol. 4:197-207 (1990)). Surprisingly, this primer set was successfully used in amplifying uniquely-sized DNA products from not only Candida albicans, but from Candida glabrata, Candida parapsilosis, and Candida tropicalis as well (see FIG. 1). These four Candida species are responsible for more than 90% of all neonatal infections caused by Candida (Butler *Pediatr. Clin. North Am.* 35:543-63 (1988), Faix, J. Pediatr. 105:616-22 (1984)). Subsequent DNA sequencing of the amplified products resulted in the design of four species-specific DNA probes which, when used in conjunction with Southern blot analysis, for example, allowed for the detection of as few as 10 organisms in 100 $\mu l$ of plasma of either Candida albicans, Candida glabrata, Candida parapsilosis or Candida tropicalis.

In a retrospective study of 14 children or neonates with culture proven candidemia, the PCR and culture results were identical in 24 of the 25 blood samples tested (see Table 2). In summary, the PCR based assay permits both the detection and speciation of the four major medically relevant Candida species from blood samples using a single primer pair. This high degree of correlation between PCR and culture will be helpful to the clinician in diagnosing systemic Candidiasis using PCR as accurately as culture methods but with greater sensitivity and rapidity.

Initially, the double-stranded DNA genome of Candida is denatured in order to break the hydrogen bonds holding the double-stranded DNA together, resulting in two single strands of DNA. The two DNA primers are added along with all of the other PCR reagents for DNA amplification to occur resulting in two identical double-stranded DNA products being made.

In view of the above, the present invention includes two DNA oligonucleotides or primers which, in combination, amplify a portion of the genome of four species of Candida. The oligonucleotides or primers comprise the sequences 5'-CGCCTCTTGATGGTGATGAT-3' (SEQ (See SEQ IDNO:1)) and 5'-TCCGGTAT-CACCTGGCTC-3' (See SEQ IDNo: 2). The Candida species that are amplified using this primer set are Candida albicans, Candida glabrata, Candida tropicalis, and Candida parapsilosis.

The present invention also encompasses four species-specific DNA probes having the following DNA sequences: 5'-CGTTCGTAC-TAGAGTTGTGTTGTTTTGGAT-3' (See (SEQ ID NO:3), 5'-CGACTGGTTGACGATAATCAGAG-GAGATGGG-3' (See SEQ ID NO:4) 5'-GAGGCTGTGATGTGTGCTGTTGACCAG-3' (See SEQ ID NO:5) and 5'-AGGCTTGCTCTTTGTCGGGCGAGCGAACG-3' (See SEQ ID NO:6). Each sequence hybridizes to an internal portion of the amplified chitin synthase 1 gene of Candida albicans, Candida glabrata, Candida parapsilosis, and Candida tropicalis, respectively.

The present invention also includes a method of diagnosing a species of Candida in a patient, causing an infection. The method includes the steps of: i) collecting a blood sample from the patient; ii) separating out the plasma and the buff coat layer fractions present in the blood sample; iii) enzymatically digesting non-yeast DNA present in the remaining fractions; iv) enzymatically digesting the cell wall of yeast present in the remaining fractions in order to release DNA present in the cells; v) extracting, precipitating and resuspending the DNA; vi) adding primers having the following sequences to the resuspended DNA: 5'-CGCCTCTTGATGGTGATGAT-3' (See SEQ ID NO:1) and 5'-TCCGGTATCACCTGGCTC-3' (See SEQ ID NO:2); vii) maintaining the primers and the resuspended DNA under conditions such that hybridization and amplification occur; and viii) comparing the length of the resulting double-stranded DNA products of step (vii) to a measured double-stranded DNA genome template obtained from Candida albicans, Candida glabrata, Candida tropicalis and Candida parapsilosis, thereby determining the species of Candida causing the infection in said patient. Again, the species of Candida which may be detected is selected from the group consisting of: Candida albicans, Candida glabrata, Candida tropicalis, and Candida parapsilosis.

Additionally, the present invention includes another method of diagnosing a species of Candida in a patient by use of species-specific probes. This method may also be used to confirm the species of Candida detected by the above-method.

In particular, this second method includes: i) denaturing the double-stranded DNA products of step (viii) of the above-method; ii) linking the resulting, denatured DNA to a membrane; iii) adding Candida species-specific probes labelled at their 3' end, to the linked, denatured DNA; iv) maintaining conditions sufficient for hybridization to occur between said denatured DNA and the probes; v) adding antibody against the label, wherein the antibody is conjugated to an enzyme; vi) adding substrate which is acted upon by the enzyme, thereby forming a measurable product; vii) measuring the product, said measurement being compared to known measurements for Candida albicans, Candida glabrata, Candida tropicalis, and Candida parapsilosis, thereby diagnosing or confirming the species of Candida present in the patient. The probes may be labeled with digoxigenin-ddUTP, for example. Furthermore, the enzyme of step (v) may be alkaline phosphatase and the substrate of step (vi) may be Lumi Phos 450. Again, the species to be detected or confirmed is selected from the group consisting of: Candida albicans, Candida glabrata, Candida tropicalis, and Candida parapsilosis.

Additionally, the present invention includes a kit for diagnosing a species of Candida causing an infection in a patient comprising:

two primers having the following DNA sequences: 5'-CGCCTCTTGATGGTGATGAT-3' and 5'-TCCGGTATCACCTGGCTC-3'. Once again, the Candida species to be diagnosed is selected from the group consisting of Candida albicans, Candida glabrata, Candida tropicalis, and Candida parapsilosis.

The present invention also includes a kit for diagnosing or confirming a species of Candida causing an infection in a patient comprising:

two primers having the following DNA sequences: 5'-CGCCTCTTGATGGTGATGAT-3' (See SEQ ID NO:1) and 5'-TCCGGTAT-CACCTGGCTC-3' (See SEQ ID NO:2) and four Candida species-specific probes having the following DNA sequences: 5'-CGTTCGTAC-TAGAGTTGTGTTGTTTTGGAT-3' (See SEQ ID NO:3), 5'-CGACTGGTTGACGATAAT-CAGAGGAGATGGG-3' (See ID NO:4) 5'-GAGGCTGTGATGTGTGCTGTTGACCAG-3' (See SEQ ID NO:5) and 5'-AGGCTTGCTCTTTGTCGGGCGAGC-GAACG-3' (See SEQ ID NO:6)

wherein the DNA sequences of said species-specific probes hybridize to a portion of the DNA of Candida albicans, Candida glabrata, Candida parapsilosis, and Candida tropicalis, respectively.

All U.S. patents and publications referred to herein are hereby incorporated by reference.

BRIEF DESCRIPTION OF THE DRAWINGS

FIG. 1 represents PCR amplification of four Candida species using one primer pair. Lane 1: DNA from Candida albicans; Lane 2: DNA from Candida parapsilosis; Lane 3: DNA from Candida tropicalis; Lane 4: DNA from Candida glabrata; Lane 5: No DNA (negative control); and Lane 6: molecular weight marker DNA.

DETAILED DESCRIPTION OF THE INVENTION

Figure 2A:
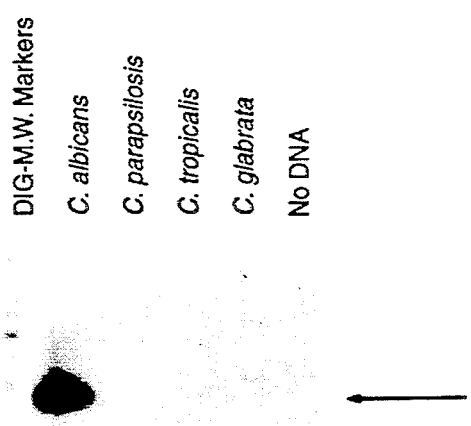
FIG. 2 represents four species-specific DNA probes used in the identification and confirmation of PCR amplified products from Candida albicans, Candida glabrata, Candida parapsilosis, and Candida tropicalis.

The Chitin synthase (CHS1) gene was selected for PCR amplification for the following reasons:

First, its gene product is clinically relevant, as it is the enzyme responsible for synthesizing chitin, the major cell wall component found in yeast, and the enzyme is upregulated in the filamentous pseudohyphae, the structure involved in tissue invasion. Braun and Calderone reported that chitin synthase levels are twofold higher from the filamentous phase of Candida albicans as compared to its yeast phase (J. Bacteriol 133:1472–77 (1978)).

Secondly, the chitin synthase gene is yeast-specific, having no mammalian, bacterial, or viral counterpart. This is an important point in avoiding false positive amplification of mammalian DNA which will be present in these clinical samples.

More specifically, patients' blood samples contain nucleated cells, a source of a person's own DNA. Thus, this DNA will be co-extracted with yeast DNA during sample preparation for PCR analysis. Consequently, one does not want to amplify a yeast gene that has a mammalian homolog since one cannot separate mammalian DNA from "infectious" DNA.

Finally, the region within the CHS1 gene selected for amplification contains no homology to Saccharomyces cereviSiae, the common bakers' and brewers' yeast, and the organism used to initially clone its homolog from Candida albicans. Based on this rationale, a set of primers was designed from sequence information provided by Au-Young (Mol. Microbiol. 4: 197-207 (1990)) to amplify a 122 base pair product of the Candida albicans chitin synthase 1 gene. In further testing, this primer pair was successfully used to amplify DNA templates of Candida glabrata, Candida parapsilosis, and Candida tropicalis as well (FIG. 1). The four species represent over 90% of all neonatal infections caused by Candida.

In constructing a set of primers for PCR amplification, one primer must hybridize to one strand of DNA, and the other must hybridize to the opposite strand. The terms "coding" and "noncoding" (see below) come from the fact that the "coding" strand of DNA is read by the RNA polymerase during transcription to make messenger RNA. The "noncoding" strand of DNA is not "transcribed" by RNA polymerase. In other words, it does not code for a messenger RNA or a protein. It is the complement of the coding strand.

The sequences of the primer pair of the present invention are as follows:
Common Primers:
Coding (base pair #2039-2058): 5'-CGCCTCTTGATGGTGATGAT-3' (See SEQ ID NO:1).
Noncoding (base pair #2161-2143): 5'-TCCGGTATCACCTGGCTC-3' (See SEQ ID NO:2).

These primers do not amplify DNA purified from Candida krusei, candida guilermondii, Candida lusitaniea, Saccharomyces cerevisiae, Escherichia coli, Klebsiella pneumonias, Pseudomonas aeruginosa, Staphylococcus aureus, Beta-hemolytic Streptococcus group A and B, Streptococcus faecalis, Haemophilus influenza, Staphylococcus epidermidis, Neisseria gonnoherrea, and Bacillus fragilis (see Table 1 below). These results indicate that the PCR primer pair used for DNA amplification demonstrates a good level of specificity.

TABLE 1

THE RESULTS OF CHSI PRIMER PAIR DRIVEN PCR AMPLIFICATION OF PURIFIED DNA

| DNA SOURCE | PCR PRODUCT SIZE (bp) |
| --- | --- |
| Candida albicans | 122 |
| Candida alabrata | 550 |
| Candida paransilosis | 350 |
| Candida trodicalis | 525 |
| Candida krusei | no product generated (np) |
| Candida guilermondii | np |
| Candida lusitaniea | np |
| Saccharomyces cerevisiae | np |
| Escherichia coli | np |
| Klebsiella Rneumoniae | np |
| Pseudomonas aeruginosa | np |
| Haemophilus influenza | np |
| Neisseria gonnoherrea | np |
| Bacteroides fraailis | np |
| Staphylococcus aureus | np |
| Staphylococcus epidermidis | np |
| Beta-hemolytic Streptococcus Group A | np |
| Beta-hemolytic Streptococcus Group B | np |
| Streptococcus faecalis | np |

Using the above set of primaers (i.e., 5'-CGCCTCTTGATGGTGATGAT-3' (See SEQ ID NO:1) and 5'-TCCGGTATCACCTGGCTC-3' (See SEQ ID NO:2), the PCR amplified products of the four Candida species were distinctly different in size from one another generating a species-specific fingerprint on an agarose gel. In order to determine whether various strains and clinical isolates of the same Candida species would consistently generate the same sized PCR amplified fragment, 44 different Candida albicans isolates, 25 Candida glabrata isolates, 20 Candida tropicalis isolates, and 19 Candida parapsilosis isolates were tested. In every case, the purified DNA from each isolate of the same species generated an identically-sized product after PCR amplification as the American Type Culture Collection (ATCC) strain (data not shown). Therefore, this CHS1 primer pair is ideally suited to be used to consistently amplify and speciate the four major clinically relevant Candida species in a single PCR assay.

Again, it is important to note that this one set of primers will amplify DNA from C. albicans, C. glabrata, C. parapsilosis, and C. tropicalis. The PCR amplified DNAs are all different in size even though the same primer is used for the four different species. If the concentration of DNA is high enough, after PCR amplification, visible bands are seen on an ethidium-stained agarose gel. The sizes of the DNA fragments are compared to positive controls for each yeast species run on the same gel. As a confirmation, and for those samples where the DNA concentration is below a certain amount and not visible, the DNA from these gels can be transferred to membranes (referrred to as Southern blotting technique) and hybridized with a species-specific DNA probe in order to visualize the amplified product.

Figure 2B:
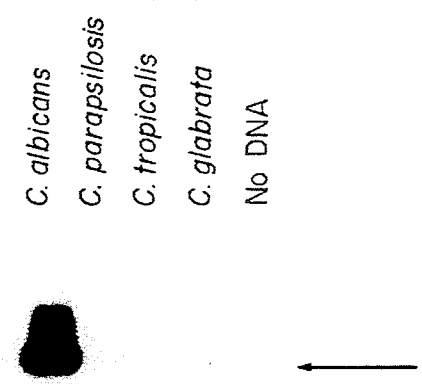
Figure 2C:
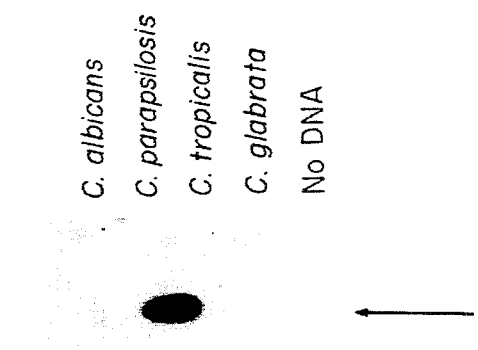
Figure 2D:
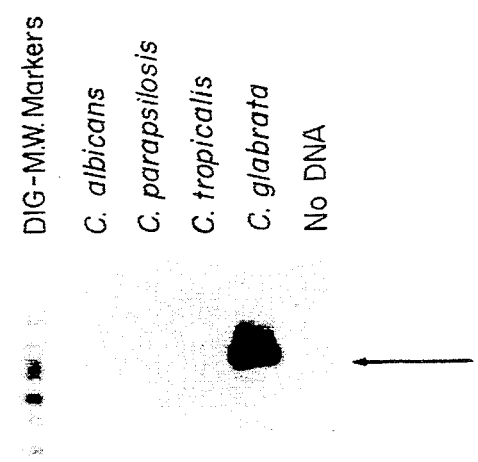

The published sequence of the Candida albicans CHS1 was also used in designing a DNA probe for detection and confirmation of the Candida albicans PCR amplified product. This probe, recognized the 122 base pair fragment amplified from Candida albicans DNA and did not hybridize to amplify DNA generated from Candida glabrata, Candida parapsilosis, or Candida tropicalis templates (FIG. 2). Therefore, additional probes were required to provide an assay with similar levels of sensitivity as for Candida albicans.

To avoid false-positive signals, the DNA probes designed to be used for hybridization with PCR generated products need to lack any sequence homology with the primer pair used in the amplification assay. Thus, sequences internal to the two primers were utilized to design the initial probe. A probe of approximately 30 bases in length, under stringent hybridization conditions, ensures a good level of specificity.

As noted above, the initial probe did not recognize C. glabrata, C. tropicalis or parapsilosis amplified DNA. Thus, these amplified DNAs were run on a gel, the product was cut out of the gel, and the DNA was purified. This purified DNA was subsequently sequenced using the dideoxy nucleotide sequencing method. Determining this sequence information made it possible to: 1) create a species-specific probe and to 2) compare its sequence to DNA sequences within Genebank to look for homologous genes. This was done for all non-albicans species discussed in this application in order to determine that the "closest" fit in terms of DNA homology to pre-existing sequences in Genebank. The DNA sequences from all 3 species gave closest homology to the chitin synthase 1 gene of Candida albicans. This is substantial evidence to indicate that the two primers are indeed amplifying the homologous CHS1 gene in C. glabrata, parapsilosis and C. tropicalis.

The sequences of the four species-specific probes are as follows:

Species-Specific Probes:

Candida albicans: (base pair #2070-2099) 5'-CGTTCGTACTAGAGTTGTGTTGTTTTGGAT-3' (See SEQ ID NO:3)

Candida glabrata: 5'-CGACTGGTTGAC-GATAATCAGAGGAGATGGG-3' (See SEQ ID NO:4)

Candida parapsilosis: 5'-GAGGCTGT-GATGTGTGCTGTTGACCAG-3' (See SEQ ID NO:5)

Candida tropicalis: 5'-AGGCTTGCTCTTTGTCGGGCGAGCGAACG-3' (See SEQ ID NO:6). All of the probes confirm the specificity of the PCR product.

The probes could be very useful to investigators for the study of the CHS1 gene in other Candida species at a basic scientific level with respect to, for example, gene expression and regulation as well as enzyme structure and regulation.

The method of using the primers and the probes will be described, in detail, below. However, basically, when the primers are utilized for diagnostic purposes:

Blood is collected from the patient and centrifuged in order to separate the blood into 3 layers (i.e., the red blood cells, the buffy coat and the plasma). The plasma and the bully coat layer are then collected and treated with a detergent. The resulting product is then treated with, for example, an enzyme such as DNase I, in order to digest any non-yeast DNA which may be present. The chitin cell wall of the yeast is then digested, using Zymolase, for example, in order to release the yeast DNA for analysis. The DNA is then freed from bound protein by using, for example, Proteinase K digestion followed by detergent treatment. The DNA is then extracted by using phenol, for example, and then precipitated by using a chemical such as ethanol, for example. Subsequently, the DNA pellet is resuspended in distilled water. One is then ready to analyze the sample using the primers.

In particular, a portion (e.g., 1 $\mu$l) of the sample is added to a PCR master mix (e.g., 49 $\mu$l). The mix contains both primers as well as deoxynucleotides (i.e., dATP, dCTP, dGTP, dTTP), and for example, buffer, magnesium chloride, and Taq polymerase. Several cycles of PCR amplification (e.g., 30) are carried out. (First the DNA must be denatured (e.g., at 94° C. for 1 min.), the primers must anneal (e.g., at 55° C. for 2 min.) and elongation and DNA synthesis must be allowed to occur (e.g., at 72° C. for 1 min.).)

After the DNA-yeast-specific product is made, it is then analyzed on agarose gel.

It should also be noted that all of the PCR "runs" contain 4 positive controls (i.e., one each of C. albicans, C- parapsilosis, C. tropicalis, and C. glabrata template DNA (see FIG. 1)). Several negative controls are also run. NO DNA is added to these tubes, so no DNA product should be made. In addition, digoxigenin-labeled DNA molecular weight standards are run along side the clinical samples and controls on the agarose gel as a molecular weight marker to estimate the sizes of the DNA fragments that were generated by PCR.

In order to utilize the probes for diagnostic and confirmatory purposes, the following steps are carried out:

The DNA separated onto an agarose gel is denatured and blotted onto a nylon membrane where it is permanently linked. Samples are then run in quadruplicate so that all four probes can be analyzed individually.

This denatured DNA exists as single-stranded DNA and is available to hydrogen bond (i.e., hybridize) to a single-stranded DNA probe.

Species-specific probes are then individually used. These DNA probes are 3' end-labelled with, for example, a digoxigenin labeled ddUTP, using $T_4$ terminal transferase, for example. The labeled probes are then added to the DNA-containing blots and, subsequently, the following reagents are added: antibody to digoxigenin (or label utilized) which is conjugated to an enzyme, for example, alkaline phosphatase.

Substrate is then added which the enzyme converts to a measurable product. The substrate may be Lumi Phos 450 which emits light that is detected if a piece of X-ray film is put down on the blot for approximately 10-20 minutes. The X-ray film is then developed to give a signal (see FIG. 2).

These probes are used for confirmation purposes, and provide evidence that the "correct" sized PCR product is also yeast specific. The use of DNA probes also provides a much more sensitive assay, as this assay will detect a product which is not visible upon ethidium bromide staining of the agarose gel.

The present invention can be illustrated by the use of the following non-limiting examples:

Example I

Synthesis of the Primers

Specimen Processing:

Ethylenediaminetetraacetic (EDTA) containing whole blood samples were processed in a manner similar to that described by Buchman et al. (Surgery 108:338-47 (1990)). Briefly, 100 $\mu$l to 1 ml volumes of EDTA containing whole blood was collected by venipuncture or obtained from central lines of patients with culture proven Candidiasis. These blood samples were collected as soon as possible after the blood cultures became positive. The red cells in the specimens were pelleted by centrifugation (2 min at 13,000 x g), and the combined plasma and buffy coat fractions collected. The fractions were treated with an equal volume of a non-ionic detergent cocktail containing 1% Tween-20 and 1% NP-40 dissolved in 50 mM TRIS buffer pH 7.5. After centrifugation (13,000 x g for 2 min), the pellets were resuspended in a non-ionic detergent cocktail containing 0.5% Tween-20 and 0.5% NP-40 in 50 mM TRIS buffer pH 7.5. The resulting pellets were washed twice in 50 mM TRIS buffer pH 7.5 containing 10 mM MgCl and treated with DNase I at a concentration of 10 mg/ml for 15 minutes at 37° C. The DNase I enzyme was subsequently inactivated by adding EDTA to a final concentration of 10 mM and heating to 85° C. for 30 minutes. Any yeast cells present within the samples were pelleted by centrifugation at 13,000 x g for 10 min., and their cell walls digested using a yeast digestion buffer consisting of 300 mg/ml Zymolase in 50 mM TRIS buffer pH 7.5 containing 10 mM EDTA and 28 mM Betamercaptoethanol. Specimens were incubated for 1 hour at 37° C. before adding sodium dodecyl sulfate (SDS) and Proteinase-K (PK) to final concentrations of 0.1% and 15 mg/ml respectively. The samples were incubated for 5 minutes at 37° C. before being boiled for 5 minutes, quick chilled, and the DNA extracted once in an equal volume of buffer saturated phenol and chloroform/isoamyl alcohol (24:1), once with an equal volume of chloroform-isoamyl alcohol alone and finally precipitated in 2.5 volumes of 100% ethanol. Each DNA pellet was resuspended in 25 ul sterile dH$_2$O and a 1 ul sample amplified by PCR.

Preparation of Control DNA:

Single colonies of the ATCC strains of Candida albicans, Candida glabrata, Candida parapsilosis, and Candida tropicalis were inoculated into 1 ml broth cultures of brain heart infusion and incubated at 37° C. for 24–28 hours. The cultures were then centrifuged for 2 mins. at 13,000 x g to pellet the yeast. These pellets were resuspended in 100 µl volumes of 50 mM TRIS HCl pH 7.5 containing 10 mM EDTA and 28 mM Beta-mercaptoethanol containing 300 µg/ml of the yeast lytic enzyme Zymolase. Samples were incubated at 37° C. for 1 hr. to prepare spheroplasts. The spheroplasts were solubilized by adding SDS and PK to final concentrations of 0.1% and 15 µg/ml, respectively for 5 min. at 37° C., and then boiled for 5 mins. at 95° C. to inactivate the PK. Samples were quick chilled on ice and the DNA extracted using equal volumes of buffer saturated phenol and chloroform isoamyl alcohol (24:1) and once in an equal volume of chloroform isoamyl alcohol alone. The nucleic acid within the aqueous phase of the samples was precipitated with the addition of one-half volume 7.5 M ammonium acetate and 3 volumes of ice cold 100% ethanol following 30 min. at −80° C. and pelleted by centrifugation at 13,000 x g for 15 mins. at 4° C. The resulting DNA pellets were washed in ice cold 70% ethanol and resuspended in 25 µl of sterile distilled water prior to amplification.

PCR Amplification Strategy:

Each reaction for PCR amplification contained 1 µl of extracted DNA template from clinical samples or control organisms and 49 µl of the following PCR master mix: 5 µl of a 10x PCR buffer containing 20 mM magnesium chloride, 8 µl of a 200 µM deoxynucleotide triphosphate (dNTP) mixture (equimolar amounts of dATP, dCTP, dGTP and dTTP), 1 µl of a 20 mM stock of each CHS1 primer, and 1.25 Units of AmpliTaq polymerase. Large batches of the PCR master mix containing the TRIS buffer, magnesium chloride, dNTPs and primers (excluding the AmpliTaq polymerase) were stored in small individual use aliquots at −20° C., thawed, used once and then discarded. This procedure helps prevent contamination problems as well as assay consistency problems. Positive displacement pipettes were used in preparing and aliquoting the PCR master mix and when adding the clinical sample to the reaction mixture. A 50 µl overlay was then added to each tube before placing them in the 480 Series Perkin-Elmer Cetus thermocycler. Thirty cycles of a threestep amplification process were run including 94° C. for 1 min., 54° C. for 2 mins. and 72° C. for 1 min; followed by 7 mins. extension time at 72° C. to complete the assay. Twenty microliters of each sample were analyzed in quadruplicate on a 1% LE agarose/3% NuSieve agarose gel in lx TAE buffer. Each batch of samples analyzed must also include the four positive control DNA templates and negative control samples (tubes lacking template DNA). The agarose gel containing the amplified DNA is then treated with 0.4 M sodium hydroxide and 0.6 M sodium chloride for 30 mins. to obtain single stranded DNA for overnight transfer to a nylon membrane (Gene Screen Plus, Dupont) in the same denaturing solution.

On the next day, the nylon membrane was neutralized in 0.5 M TRIS-HCl, pH 7.0 and 1 M sodium chloride for 15 mins. before the DNA was UV-crosslinked onto the membrane in preparation for hybridization with the 4 species-specific probes: one for C. albicans, C. glabrata, C. parapsilosis, and C. tropicalis.

Example II

Detection of PCR Amplified DNA Products Using

Species-Specific Probes Labelled with Digoxigenin Linked ddUTP

In addition to the probe designed from the published sequence of C. albicans, three probes were designed after the entire sequence of each PCR amplified product was determined. The individual PCR generated fragments of Candida albicans, Candida glabrata, Candida parapsilosis, and Candida tropicalis were cloned into pCR-Script SK(+) vector using T$_4$ directed blunt end ligation (catalog #211190 Stratagene, LaJolla, Calif.). The flanking T$_3$ and T$_7$ promoters and primers were used in conjunction with Sequenase Version 2.0 DNA sequencing kit to determine the sequence of the PCR inserts (USB, Cleveland, Ohio). As a result, four species-specific probes are available to provide maximal sensitivity for detecting Candida albicans, Candida glabrata, Candida parapsilosis, and Candida tropicalis using a single primer pair.

Each species-specific DNA probe is 3' end-labeled with digoxigenin-ddUTP (DIG-ddUTP) using the enzyme Terminal Transferase according to the manufacturer's directions (Boehringer Mannheim).

In terms of sensitivity, the PCR assay, in conjunction with Southern blot analysis using digoxigenin-ddUTP labeled probes and a chemiluminescent detection system, was able to detect between 10–100 colony forming units per milliliter (CFU/ml) of Candida albicans. This level of sensitivity was also true for the other three Candida species mentioned (data not shown). The sensitivity of the assay was determined by adding known amounts (CFU/ml) of Candida albicans to 1 ml volumes of EDTA containing whole blood, and the DNA extracted from each sample was amplified and detected as described in Example I.

Example III

A Retrospective Study Comparing PCR to Culture for Identifying Candida in Blood

In a retrospective study of 14 children or neonates with culture-proven candidemia, the PCR and culture results were identical in 24 of 25 blood samples tested (Table 2). In this study sample, volumes from between 0.2 to 1 ml of EDTA containing the whole blood was collected from neonates or children documented to have culture-proven candidemia. Twenty-four of the 25 blood samples analyzed by PCR were collected prior to initiation of anti-fungal therapy. However, in the one case in which the blood culture grew Candida albicans and the PCR results were negative, the blood sample for PCR analysis was not collected until after 5 days of amphotericin-B therapy. These results strongly suggest that this PCR-based assay permits both identification and speciation of the four major medically relevant Candida species in less time than conventional culturing. This high degree of correlation and decreased turnaround time for Candida identification using PCR instead of culture will be helpful in better assisting the clinician in diagnosing systemic candidiasis.

to alkaline phosphatase enzyme and is deteected by addition of a colorimetric substrate.

TABLE 2

| PATIENT | # OF BLOOD SAMPLES | CULTURE RESULTS | PCR RESULTS |
|---------|-------------------|-----------------|-------------|
| 1 | 2 | C. albicans | C. albicans |
| 2 | 2 | C. albicans | C. albicans |
| 3 | 2 | C. albicans | C. albicans |
| 4 | 2 | C. albicans | C. albicans |
| 5 | 2 | C. albicans | C. albicans |
| 6 | 1 | C. albicans | Negative* |
| 7 | 2 | C. albicans | C. albicans |
| 8 | 2 | C. albicans | C. albicans |
| 9 | 1 | C. glabrata | C. glabrata |
| 10 | 2 | C. parapsilosis | C. parapsilosis |
| 11 | 2 | C. parapsilosis | C. parapsilosis |
| 12 | 1 | C. parapsilosis | C. parapsilosis |
| 13 | 2 | C. parapsilosis | C. parapsilosis |
| 14 | 2 | C. tropicalis | C. tropicalis |

*Blood sample for PCR analysis was taken 5 days after initiation of anti-fungal therapy.

EXAMPLE IV

Use of the Primers for Detecting Candidiasis in High Risk Neonates on Steroids and Hyperalimentation Therapy Twenty-nine blood samples (100 µl of EDTA containing blood) were collected on neonates considered at high risk for developing fungemia based on their use of hyperalimentation and/or steroid therapies. These high-risk neonates, however, were without suspicion of infection.

The 29 blood samples were analyzed for the presence of Candida DNA as described above. All 29 samples were negative by PCR for Candida. This study proved that one does not pick up or detect the presence of Candida which may be just colonizing the skin's surface.

EXAMPLE V

Two Additional Approaches of Carrying Out Detection and/or Confirmation of the Four Species of Candida The four Candida probes cloned into pCR-Script vector also allow for the synthesis of RNA-based transcripts which can be used in another type of a detection system for PCR-generated DNA products. This detection process eliminates gel blots and involves the use of the enzyme linked immunosorbent assay (ELISA) assay and the Digene Diagnostic, Inc. system.

Approach 1:

The primer is labeled at the 5' end with biotin. All 4 Candida species PCR fragments are cloned into pCR-Script in order to generate RNA probes. Ninety-six well plates are coated with Strep-Avidin.

Biotinylated primer is incorporated into the PCR product. This double-stranded DNA is then denatured to give single strands, and the strands are hybridized to the species-specific RNA probe. This RNA/DNA (biotin) hybrid is "captured" by having a very high affinity for Strep-Avidin.

The specific RNA/DNA linked to StrepAvidin is then recognized by an antibody which recognizes RNA/DNA based hybrids. This antibody is conjugated Approach 2:

Reagents: Strep-Avidin coated 96 well plates, biotin labelled primer, digoxigenin-labeled probe, chemiluminescent substrate.

The amplified DNA product contains biotin. The PCR generated DNA is denatured to give single-stranded DNA. The denatured DNA hybridizes with the digoxigenin-labeled DNA probe (in quadruplicate (i.e., one reaction for each species-specific probe)). The $DNA_{(biotin)}/DNA_{(dig)}$ hybrid is added to the Strep-Avidin coated wells where the biotin labeled PCR generated DNA binds to the Strep-Avidin. An anti-digoxigenin antibody is added to the wells containing the bound $DNA_{(biotin)}/DNA_{(dig)}$ hybrid. The chemiluminescent substrate is added to react with the DIG/DIG antibody complex.

The DIG-labeled DNA probe alone does not bind to Strep-Avidin, so no false-positive reactions are obtained.

The biotin labeled primers alone can bind to the Strep-Avidin coated plates but do not cause a substrate change because the antibody conjugated enzyme is to digoxigenin not to biotin. Thus, no false-positive results are obtained.

EXAMPLE VI

Modification of Clinical Specimen Processing

In order to shorten processing time, zirconium beads may be added to the plasma/buffy coat layer, and the mixture is "beat-up" on the Microbead beater (Biospec Products) for three 2 minute cycles. The beads are then pelleted, and the released yeast DNA (from the fluid-containing broken yeast cell) is phenol extracted as described above, EtOH precipitated, and a microliter volume is PCR amplified. This modification eliminates detergent treatment, DNAase and Zymolase treatment. It is quicker to perform than the gel-Southern blot format, and there is less of a chance of contamination.

What is claimed is:

1. DNA oligonucleotide primers which, in combination, amplify a portion of he genome of a species of Candida, having the sequences 5'-CGCCTTGATGGTGATAGAT-3' (SEQ ID NO:1:) and 5'-TCCGGTATCACCTGGCTC-3' (SEQ ID NO:2:).

2. The DNA sequences of claim 1, wherein said Candida species is selected from the group consisting of Candida albicans, Candida glabrata, Candida tropicalis, and Candida parapsilosis.

3. A DNA species-specific probe having a DNA sequence selected from the group consisting of 5'-CGTTCGTACTAGAGTTGTGTTGTTTTGGAT-3' (SEQ ID NO:3:), 5'-CGACTGGTTGAC-GATAATCAGAGGAGATGGG-3' (SEQ ID NO:4:), 5'-GAGGCTGTGATGTGTGCTGTTGAC-CAG-3' (SEQ ID NO:5:), and 5'-AGGCTTGCTCTTTGTCGGGCGAGCGAACG-3' (SEQ ID NO:6:)
wherein said probe hybridizes to a portion of the DNA of Candida albicans, Candida glabrata, Candida parapsilosis, and Candida tropicalis, respectively.

4. A method of detecting the presence of a species of Candida in the blood of a patient comprising the steps of:
i) collecting a blood sample from said patient;
ii) separating out the plasma and the buffy coat layer fractions present in said blood sample;
iii) enzymatically digesting non-yeast DNA present in said fractions;
iv) enzymatically digesting the cell wall of yeast present in said fractions in order to release DNA present in the cells;
v) extracting, precipitating and resuspending said yeast and non-yeast DNA;
vi) adding primers having the following sequences to said resuspended DNA: 5'-CGCCTCTTGATGGTGATGAT-3' (SEQ ID NO:1:) and 5'-TCCGGTATCACCTGGCTC-3' (SEQ ID NO:2:);
vii) maintaining said primers and said resuspended DNA under conditions such that hybridization and amplification occur to form double-stranded DNA products;
viii) comparing the length of the resulting double-stranded DNA products of step (vii) to a measured double-stranded DNA genome template obtained from Candida albicans, Candida glabrata, Candida tropicalis and Candida parapsilosis; and
ix) determining the species of Candida present in said patient based on the comparison of step (viii).

5. The method of claim 4 wherein said species is selected from the group consisting of Candida albicans, Candida glabrata, Candida tropicalis and Candida parapsilosis.

6. A method of detecting or confirming a species of Candida in the blood of a patient, causing an infection, comprising the steps of:
i) denaturing said double-stranded DNA products of step (viii) of claim 4;
ii) linking said resulting, denatured DNA to a membrane;
iii) adding Candida species-specific probes labelled at their 3' end, to said linked, denatured DNA;
iv) maintaining conditions sufficient for hybridization to occur between said denatured DNA and said probes;
v) adding antibody which specifically binds to said label, wherein said antibody is conjugated to and enzyme;
vi) adding substrate which is acted upon by said enzyme, thereby forming a measurable product;
vii) measuring said product;
viii) comparing said measurement with control measurements for Candida albicans, Candida glabrata, Candida tropicalis and Candida parapsilosis to detect or confirm the presence of said species of Candida present in said patient.

7. The method of claim 6 wherein said species-specific probes of step (iii) are labelled with digoxigenin-ddUTP.

8. The method of claim 6 wherein said enzyme of step (v) is alkaline phosphatase and said substrate of step (vi) is LUMI-PHOS 450.

9. The method of claim 6 wherein said species is selected from the group consisting of: Candida albicans, Candida glabrata, Candida tropicalis, and Candida parapsilosis.

10. A kit for detecting the presence of a species of Candida causing an infection in a patient comprising:
two primers having the following DNA sequences: 5'-CGCCTCTTGATGGTGATGAT-3' (SEQ ID NO:1:) and 5'-TCCGGTATCACCTGGCTC-3' (SEQ ID NO:2:).

11. The kit of claim 10 wherein said species is selected from the group consisting of Candida albicans, Candida glabrata, Candida tropicalis, and Candida parapsilosis.

12. A kit for diagnosing or confirming a species of Candida causing an infection in a patient comprising:
two primers having the following DNA sequences: 5'-CGCCTCTTGATGGTGATGAT-3' (SEQ ID NO:1:) and 5'-TCCGGTATCACCTGGCTC-3' (SEQ ID NO:2:),
four Candida species-specific probes having the following DNA sequences: 5'-CGTTCGTAC-TAGAGTTGTGTTGTTTTGGAT-3' (SEQ ID NO:3:), 5'-CGACTGGTTGACGATAAT-CAGAGGAGATGGG-3'(SEQ ID NO:4:), 5'-GAGGCTGTGATGTGTGCTGTTGACCAG-3'(SEQ ID NO:5:), and 5'-AGGCTTGCTCTTTGTCGGGCGAGC-GAACG-3'(SEQ ID NO:6:),
wherein the DNA sequences of said species-specific probes hybridize to a portion of the DNA of Candida albicans, Candida glabrata, Candida parapsilosis, and Candida tropicalis, respectively.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

CGCCTCTTGA TGGTGATGAT                                                                                   20

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCGGTATCA CCTGGCTC                                                                                     18

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGTTCGTACT AGAGTTGTGT TGTTTTGGAT                                                                        30

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGACTGGTTG ACGATAATCA GAGGAGATGG G                                                                      31

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAGGCTGTGA TGTGTGCTGT TGACCAG                                                                           27

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AGGCTTGCTC TTTGTCGGGC GAGCGAACG                                                                         29